US012676228B2

(12) United States Patent
Kim et al.

(10) Patent No.: US 12,676,228 B2
(45) Date of Patent: Jul. 7, 2026

(54) METHOD OF CARING FOR PSYCHOLOGICAL STATUS BASED ON BIOMETRIC INFORMATION AND APPARATUS FOR PERFORMING THE SAME

(71) Applicant: DOLBOMDREAM CO., LTD., Daejeon (KR)

(72) Inventors: Ji Hun Kim, Gyeonggi-do (KR); Cheol Jun Park, Daejeon (KR); Meen Tai Kim, Sejong (KR)

(73) Assignee: DOLBOMDREAM CO., LTD., Daejeon (KR)

( * ) Notice: Subject to any disclaimer, the term of this patent is extended or adjusted under 35 U.S.C. 154(b) by 0 days.

(21) Appl. No.: 18/250,578

(22) PCT Filed: Dec. 5, 2022

(86) PCT No.: PCT/KR2022/019582
§ 371 (c)(1),
(2) Date: Apr. 26, 2023

(87) PCT Pub. No.: WO2023/153604
PCT Pub. Date: Aug. 17, 2023

(65) Prior Publication Data
US 2024/0021292 A1     Jan. 18, 2024

(30) Foreign Application Priority Data
Feb. 11, 2022     (KR) ........................ 10-2022-0018433

(51) Int. Cl.
*G16H 20/70* (2018.01)
*A61B 5/00* (2006.01)

*A61B 5/16* (2006.01)
*G06N 20/00* (2019.01)
*G16H 40/67* (2018.01)

(52) U.S. Cl.
CPC ............. *G16H 20/70* (2018.01); *A61B 5/162* (2013.01); *A61B 5/165* (2013.01); *A61B 5/6801* (2013.01); *G06N 20/00* (2019.01); *G16H 40/67* (2018.01)

(58) Field of Classification Search
CPC ................................. G16H 20/70; A61B 5/165
See application file for complete search history.

(56) References Cited

U.S. PATENT DOCUMENTS

2013/0018837 A1* 1/2013 Lee ......................... A61B 5/165
                                                                  706/52
2014/0277235 A1* 9/2014 An ........................ A61N 1/3627
                                                                  607/17

(Continued)

*Primary Examiner* — Peter H Choi
*Assistant Examiner* — Aaisha Abdullah
(74) *Attorney, Agent, or Firm* — Revolution IP, PLLC

(57) ABSTRACT

Provided are a method and apparatus for caring for a psychological status based on biometric information. The method includes acquiring real-time biometric information of the user from a wearable device worn by the user, analyzing arousal and valence of the user based on the acquired real-time biometric information, determining a psychological status of the user based on an analysis result of the arousal and valence of the user, and generating control information including information on pressure control provided from the wearable device based on the determined psychological status of the user.

10 Claims, 9 Drawing Sheets

(56)     References Cited

U.S. PATENT DOCUMENTS

| | | | | |
|---|---|---|---|---|
| 2015/0242750 A1* | 8/2015 | Anderson | .......... | G06Q 30/0631 |
| | | | | 706/50 |
| 2017/0340257 A1* | 11/2017 | Aung | ..................... | A61B 5/024 |
| 2017/0340270 A1* | 11/2017 | Ganesh | ................ | A61B 5/4836 |
| 2020/0133622 A1* | 4/2020 | Coover | ................... | G06F 3/165 |
| 2021/0401338 A1* | 12/2021 | Flickinger | ............. | G16H 40/63 |
| 2022/0165393 A1* | 5/2022 | Inz | ....................... | A61B 5/7264 |
| 2023/0032131 A1* | 2/2023 | Harper | ................ | A61B 5/0022 |
| 2024/0090807 A1* | 3/2024 | Rus | ..................... | A61B 5/7282 |

* cited by examiner

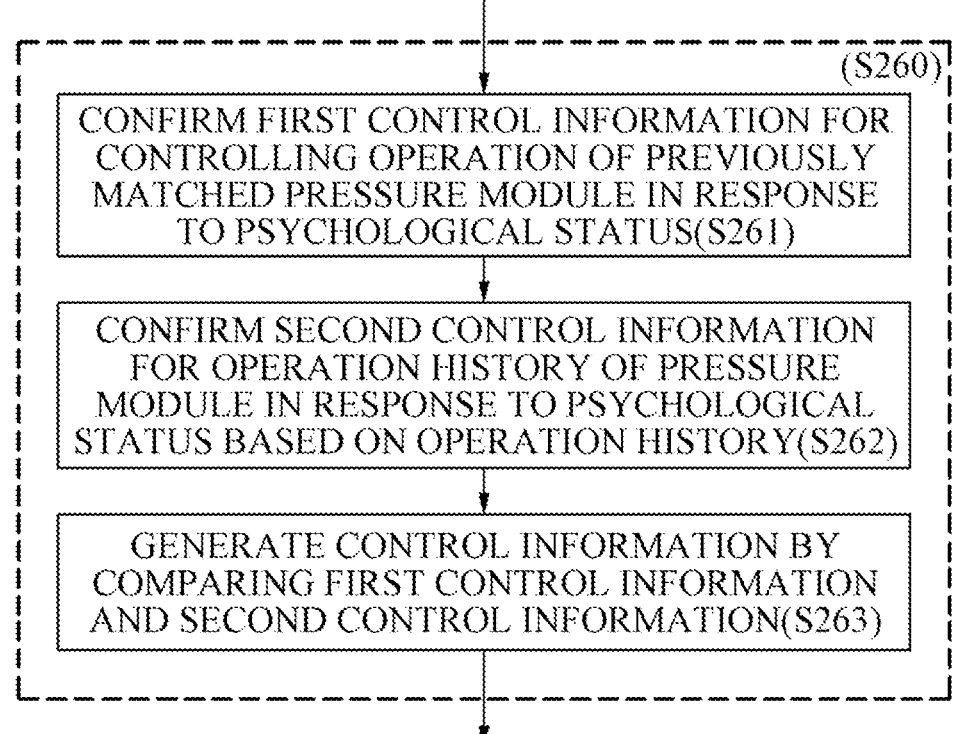

(S260)

CONFIRM FIRST CONTROL INFORMATION FOR CONTROLLING OPERATION OF PREVIOUSLY MATCHED PRESSURE MODULE IN RESPONSE TO PSYCHOLOGICAL STATUS(S261)

CONFIRM SECOND CONTROL INFORMATION FOR OPERATION HISTORY OF PRESSURE MODULE IN RESPONSE TO PSYCHOLOGICAL STATUS BASED ON OPERATION HISTORY(S262)

GENERATE CONTROL INFORMATION BY COMPARING FIRST CONTROL INFORMATION AND SECOND CONTROL INFORMATION(S263)

FIG. 5

METHOD OF CARING FOR PSYCHOLOGICAL STATUS BASED ON BIOMETRIC INFORMATION AND APPARATUS FOR PERFORMING THE SAME

TECHNICAL FIELD

The present invention relates to a method of caring for a psychological status based on biometric information and an apparatus for performing the same, and more particularly, a method and apparatus for adjusting a psychological status of a user by providing a user with appropriate psychological safety through air compression based on biometric information of the user.

BACKGROUND ART

Recently, as the importance of managing or stabilizing a human psychological status has been increasing, methods and techniques for adjusting or controlling psychology have been proposed. In particular, managing or stably maintaining psychological statuses of people in special circumstances (e.g., infants, people with autism spectrum disorder, or the elderly) is a very important part.

In this regard, as methods and techniques for determining or estimating a human psychological status, methods and techniques of obtaining biometric information, which is information related to a human body, and determining or estimating a human psychological status based on the obtained biometric information have been proposed. However, although various methods and techniques for determining or estimating a human psychological status have been proposed, there is a problem in that there are not various methods or techniques for managing or stably adjusting human psychology according to a psychological status.

In addition, in order to adjust human psychology to manage or stably maintain the human psychology according to the psychological status, there is a problem in that there is a need to visit a special location where professional equipment is pre-installed (e.g., a hospital or psychological treatment center), and there are not many methods or techniques for adjusting psychology to manage or stably maintain the psychology in real time.

DISCLOSURE

Technical Problem

The present invention is directed to providing a method and apparatus for caring for a psychological status of a user based on biometric information of the user collected through a wearable device.

In addition, the present invention is directed to providing a method and apparatus for monitoring a psychological status of a user through collection of biometric information of the user and converting the monitored psychological status of the user into big data, and adaptively adjusting the psychological status of the user using an artificial neural network-based model trained based on the adjustment of the psychological status and the biometric information of the user reacting the adjustment.

Technical Solution

One aspect of the present invention provides a method of caring for a psychological status based on biometric information that is performed by a computing device. The method may include: acquiring real-time biometric information of a user from a wearable device worn by the user; analyzing arousal and valence of the user based on the acquired real-time biometric information; determining a psychological status of the user based on an analysis result of the arousal and valence of the user; and generating control information including information on pressure control provided from the wearable device based on the determined psychological status of the user.

Advantageous Effects

A method of caring for a psychological status based on biometric information according to an exemplary embodiment can clearly determine a psychological status of a user who needs to be cared for in real time, and control the psychological status to be stabilized based on the determined psychological status through a wearable device or the like worn by the user. In addition, according to a method of caring for a psychological status based on biometric information according to an exemplary embodiment, an appropriate external force can be applied through an operation of a psychological control device so that the psychological status of the user can be stabilized based on content of a history of the operation of the psychological control device for the psychological control of the user, and furthermore, more accurate psychological status prediction and care control can be performed by utilizing an artificial neural network trained based on accumulated data.

DESCRIPTION OF DRAWINGS

FIG. 1 is a conceptual diagram illustrating an environment in which a method of caring for a psychological status based on biometric information according to an embodiment of the present invention is performed.

FIG. 4 is a flowchart illustrating a method of generating control information in the method of caring for a psychological status based on biometric information according to the embodiment.

FIG. 5 is a diagram illustrating a reaction information table of a user used in the method of caring for a psychological status based on biometric information according to the embodiment.

MODES OF THE INVENTION

Figure 2:
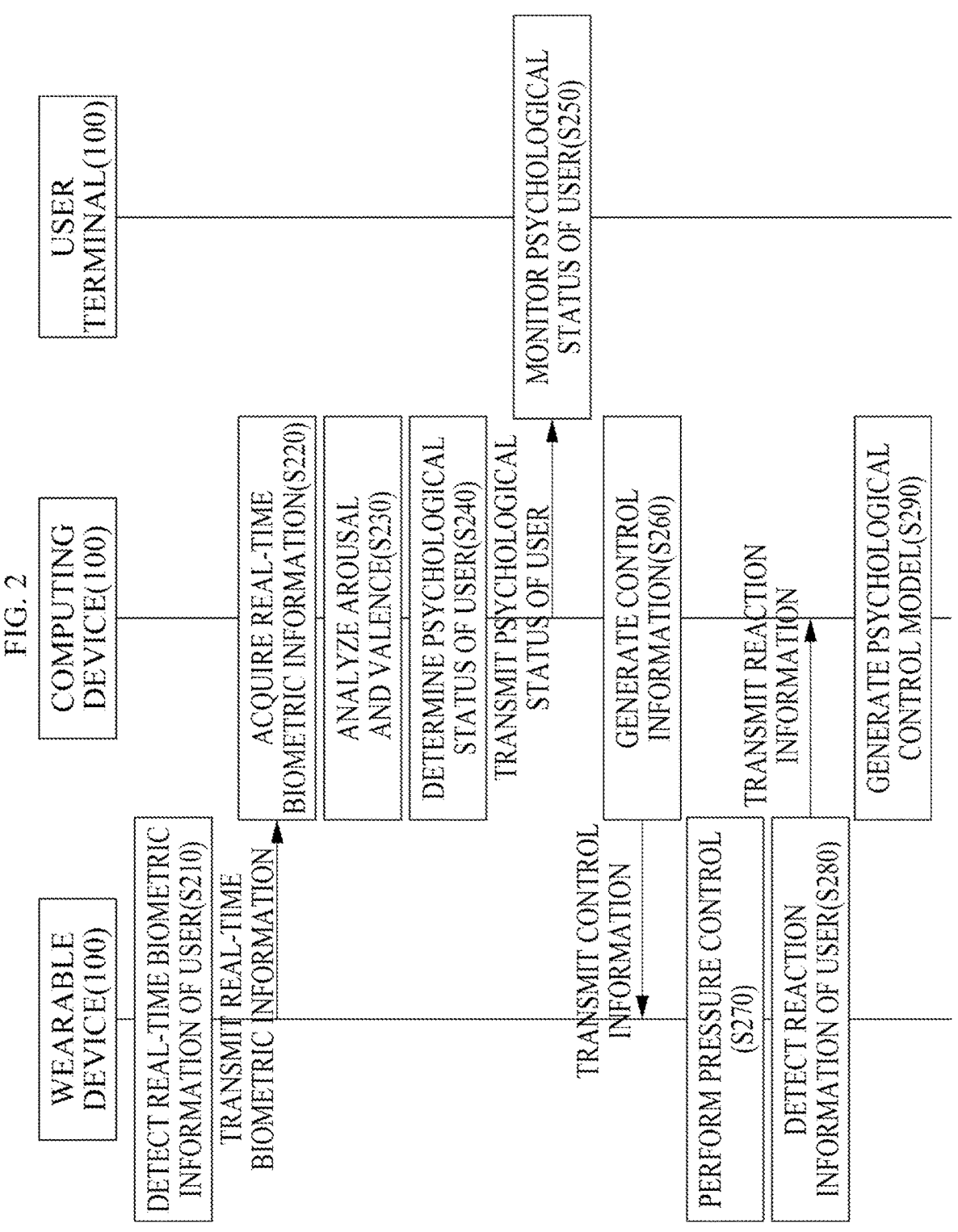
FIG. 2 is a flowchart illustrating the method of caring for a psychological status based on biometric information according to the embodiment of the present invention.

A method of caring for a psychological status based on biometric information according to an embodiment for achieving the above object is performed by a computing device. The method may include: acquiring real-time biometric information of a user from a wearable device worn by the user; analyzing arousal and valence of the user based on the acquired real-time biometric information; determining a psychological status of the user based on an analysis result of the arousal and valence of the user; and generating control information including information on pressure control provided from the wearable device based on the determined psychological status of the user.

The analyzing of the arousal and valence may include: determining the arousal based on information including, among electrodermal activity, heart rate variability, body temperature, respiration, motion, position, speed, and voice information included in the acquired real-time biometric information of the user, at least the electrodermal activity; and analyzing the valence based on information including, among the electrodermal activity, the heart rate variability, the body temperature, the respiration, the motion, the position, speed, and the voice information included in the acquired real-time biometric information of the user, at least the heart rate variability.

The determining of the psychological status of the user may include: determining, based on the analyzed arousal and valence of the user, one of a plurality of areas located within predetermined boundary values each of the valence and arousal on a two-dimensional plane having the valence and arousal as an X axis and a Y axis, respectively; and determining a predetermined psychological status corresponding to the determined one area as the psychological status of the user.

The generating of the control information may include generating control information according to the determined psychological status of the user by referring to a pre-stored control information table including control information corresponding to the psychological status of the user, and the control information may include at least one of a pressure level, pressure intensity, a pressure time, and identification information of a pressure module for the pressure control provided from the wearable device.

The method may further include: obtaining reaction information of the user from the wearable device; generating a reaction vector corresponding to the reaction information; generating a reaction history vector for each pressure level of the user based on the generated reaction vector; and generating an adjustment vector for a plurality of areas located within predetermined boundary values of each of the valence and the arousal on a two-dimensional plane having the valence and the arousal as the X and Y axes, respectively, in which the generating of the control information may include determining the control information by comparing the generated reaction history vector of the user with an adjustment vector for a area corresponding to the determined psychological status of the user among the plurality of areas.

The method may further include: acquiring reaction information of the user from the wearable device; and generating a psychological care model trained using the real-time biometric information of the user, the psychological status of the user, the control information, and the reaction information of the user corresponding thereto, in which the reaction information may include the biometric information of the user detected for a predetermined time after transmitting the generated control information to the wearable device.

The determining of the psychological status of the user may include: inputting the real-time biometric information into the psychological care model, and setting boundary values of a plurality of areas located on a two-dimensional plane having the valence and the arousal as an X axis and a Y axis, respectively; determining one of the plurality of areas divided by the determined boundary values based on the analyzed valence and arousal of the user; and determining a predetermined psychological status corresponding to the determined one area as the psychological status of the user.

The generating of the control information may include generating the control information by inputting at least one of the real-time biometric information and the determined psychological status of the user to the psychological care model, and the control information may include at least one of pressure level information, a pressure time, and identification information of a pressure module for the pressure control provided from the wearable device.

The method may further include: acquiring user information including at least one of positional information of the user and an age, a height, a weight, a sex, and a degree of disability of the user from the wearable device and a user terminal, in which the generating of the control information may include: generating a control information table including control information corresponding to the psychological status of the user based on the positional information of the user and the information of the user; and generating control information according to the determined psychological status of the user by referring to the generated control information table.

A computing device for caring for a psychological status of a user based on biometric information includes: a processor; and a memory in which at least one instruction to be executed by the processor is stored, in which the at least one instruction may be executed to perform control to: acquire real-time biometric information of the user from a wearable device worn by the user; analyze arousal and valence of the user based on the acquired real-time biometric information; determine the psychological status of the user based on an analysis result of the arousal and valence of the user; and generate control information including information on pressure control provided from the wearable device based on the determined psychological status of the user.

Since the present invention may be variously modified and have several exemplary embodiments, specific exemplary embodiments will be illustrated in the accompanying drawings and be described in detail in a detailed description. However, it is to be understood that the present invention is not limited to a specific exemplary embodiment, but includes all modifications, equivalents, and substitutions without departing from the scope and spirit of the present invention. In describing each drawing, similar reference numerals are used for similar components.

Terms such as "first," "second," "A," "B" etc. used in the specification may be used to describe various components, but the components are not to be interpreted to be limited by the terms. The terms are used only in order to distinguish one component from another component. For example, a "first" component may be called a "second" component and a "second" component may also be similarly called a "first" component without departing from the scope of the present disclosure. The term "and/or" includes a combination of a plurality of related described items or any one of the plurality of related described items.

It is to be understood that when one element is referred to as being "connected" or "coupled" to another element, it may be connected directly or coupled directly to another element or may be connected or coupled to another element with still another element intervening therebetween. On the other hand, it should be understood that when one element is referred to as being "connected directly" or "coupled directly" to another element, it may be connected or coupled to another element with no other element interposed therebetween.

Terms used in the present specification are used only in order to describe specific exemplary embodiments rather than limiting the present invention. Singular forms are intended to include plural forms unless the context clearly indicates otherwise. It will be further understood that the terms "comprise" or "have" used in this specification specify the presence of stated features, steps, operations, components, parts or combinations therefore mentioned in this specification, but do not preclude the presence or addition of one or more other features, numerals, steps, operations, components, parts, or combinations thereof.

Unless indicated otherwise, it is to be understood that all the terms used in the specification including technical and scientific terms have the same meaning as those that are generally understood by those skilled in the art. It should be understood that the terms defined by the dictionary are identical with the meanings within the context of the related art, and they should not be ideally or excessively formally defined unless the context clearly dictates otherwise.

Hereinafter, preferred embodiments according to the present disclosure will be described in detail with reference to the accompanying drawings.

Figure 1:
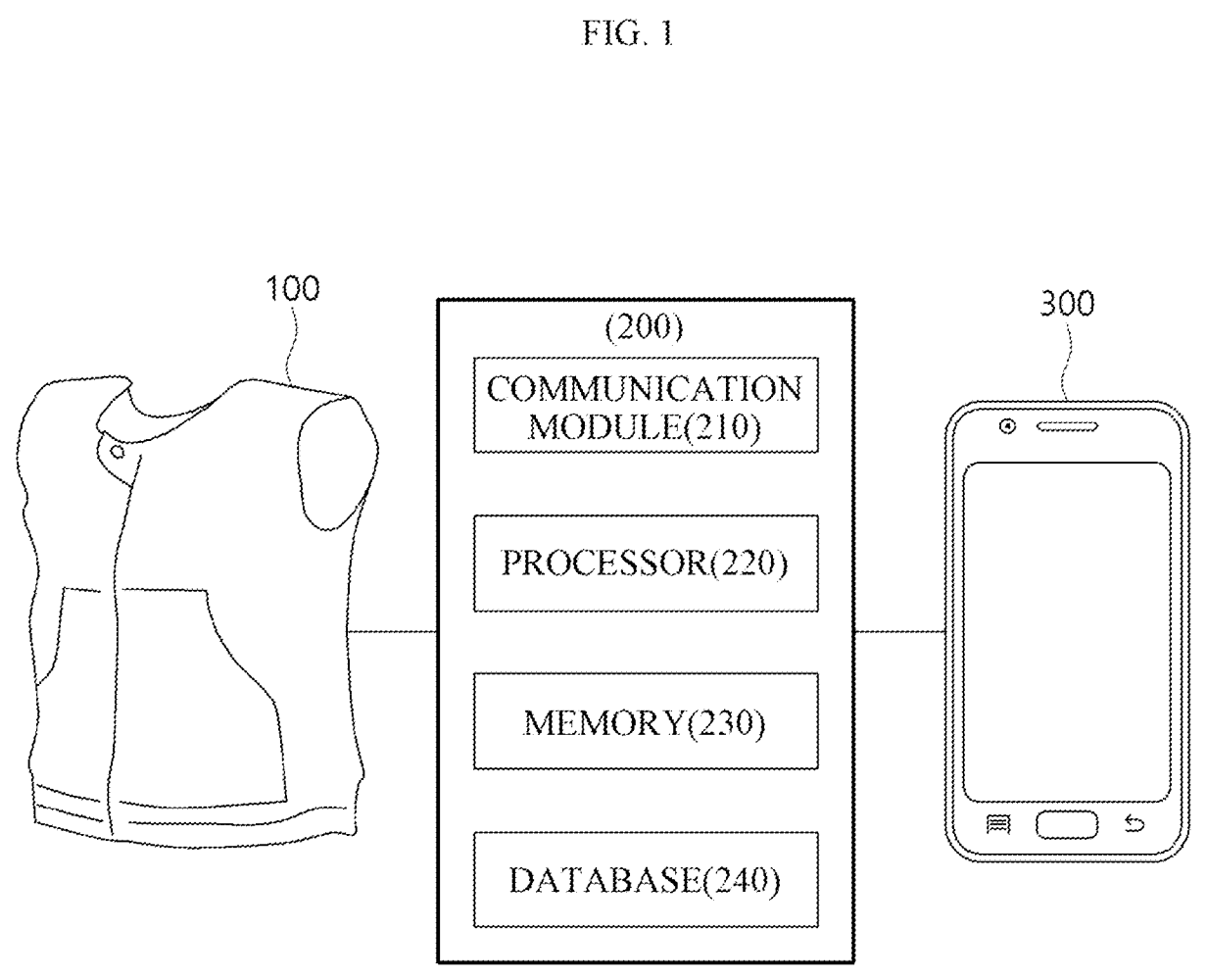

FIG. 1 is a conceptual diagram illustrating an environment in which a method of caring for a psychological status based on biometric information according to an embodiment of the present invention is performed.

Referring to FIG. 1, a method of controlling psychology based on biometric information according to an embodiment of the present invention may be performed based on a wearable device 100, a computing device 200, and a user terminal 300.

First, the wearable device 100 according to the embodiment may be a means worn by a user whose psychological status needs to be cared for, and may be a variety of wearable means capable of applying pressure to the body of the user, such as clothes and sundries that may come into contact with the body of the user. The wearable device 100 may be configured to include a sensor unit that collects various types of information that may be collected from the user wearing the wearable device, such as biometric information, and a driving unit that receives and pre-processes biometric information from the sensor unit, and receives a control signal from the computing device 200 to provide pressure for the psychological status of the user care. The sensor unit and the driving unit according to the embodiment may be connected by pairing in a wireless method such as a Bluetooth Low Energy (BLE) or wired method to transmit and receive information.

The sensor unit and the driving unit of the wearable device 100 according to the embodiment may be implemented as one component or may be implemented as separate components to transmit and receive information to and from each other, and may be implemented to be detachable from a wearing means such as a vest of the wearable device 100.

The sensor unit of the wearable device 100 according to the embodiment may include a communication module for communication with the driving unit, an electrodermal activity (EDA) sensing module, an electrocardiogram (ECG) sensing module, a photoplethysmogram (PPG) sensing module, a respiration (RESP) sensing module, a thermal sensing module, a heart rate variability (HRV) sensing module, and the like. The sensor unit may detect each piece of information in different sampling cycles and periodically transmit the detected information to the driving unit according to a predetermined cycle.

The driving unit of the wearable device 100 according to the embodiment may include a communication module for communication with the sensor unit and a communication module for communication with the computing device 200, a pre-processing module for pre-processing various information received from the sensor unit, a position tracking module (Global Positioning System (GPS)), a plurality of pressure modules serving as air pads to provide pressure, and a motor module for air injection, and further include a microcontroller unit (MCU), an inertial measurement unit (IMU), a pressure sensing module, a solenoid valve for air discharge, and the like.

The computing device 200 according to the embodiment may be a device such as a server that generates and provides a control signal for performing a method of caring for a psychological status based on biometric information, and manages and operates a service, a platform, or the like related to the psychological status care of the user. The computing device 200 may transmit and receive information required to perform the method of caring for a psychological status based on biometric information to and from the driving unit of the wearable device 100 through the communication module 210, and transmit and receive various types of information necessary for information sharing with the user terminal 300. For example, the computing device 200 and the wearable device 100 may be connected to each other based on wireless communication such as LTE-Machine Type Communication (LTE-M).

The computing device 200 according to the embodiment may include at least one processor 220 and a memory 230 storing instructions instructing the at least one processor to perform at least one operation.

Here, the at least one processor 220 may be a central processing unit (CPU), a graphics processing unit (GPU), or a dedicated processor on which methods according to the embodiments of the present invention are performed. In addition, each of the memory 230 and the database 240 may include at least one of a volatile storage medium and a non-volatile storage medium. For example, the memory 230 may include at least one of a read only memory (ROM) and a random access memory (RAM).

The database 240 according to the embodiment may store various pieces of information required to perform the method of caring for a psychological status. Basically, the database may include identification information (ID and PW) of a guardian using a user terminal, basic guardian-related information (e.g., personal information, etc.), and guardian target (user) identification information.

Also, information on a user whose psychological status needs to be cared for may include a user ID, basic user-related information (e.g., personal information, body information, etc.), a biometric information ID, and session count information. In addition, the biometric information (signal) includes information on a biometric information ID, a session count, an eye ID, sensor 1, sensor 2, sensor 3, a vest ID, a sensor ID, whether a motor is driving, pressure intensity, a start time, an end time, and the like.

In addition, the wearable device information may include a vest ID, a registration date, a remaining battery level, current pressure intensity, a size, basic information, and the like. The information on the sensor may include information on a sensor ID, a sampling rate, a registration date, and a remaining battery level. The information on the user_vest_connection may include information on a vest ID, a user ID, and a registration time which are matched with each other. In addition, the information on the sensor_vest_connection may include information on the vest ID, the user ID, the registration date, etc. which are matched with each other.

Meanwhile, the computing device 200 according to the embodiment may provide a service for monitoring and controlling a psychological status of a user to the user terminal 300, and provide the service through a monitoring application.

Specifically, the user terminal 300 is a terminal used by a user whose psychological status needs to be cared for or his or her guardian, and by installing the monitoring application, the user terminal 300 may be connected to the computing device 200 based on wireless communication and receive various platforms and services provided from the computing device 200.

The user terminal 300 according to the embodiment may provide information to a user or a guardian by displaying various types of collected information such as the biometric information and positional information of the user wearing the wearable device 100. In addition, the user terminal 300 may provide information to a user or a guardian by displaying the information on the arousal and valence and psychological status of the user determined by the computing device 200. In addition, the user terminal 300 may directly receive a control signal including information on pressure control provided from the user or guardian to the wearable device 100 through the monitoring application and transmit the control signal to the computing device 200.

In addition, the user terminal 300 according to the embodiment may acquire user information and guardian information for user registration and member management through the monitoring application.

Hereinafter, a process of performing the method of caring for a psychological status based on biometric information according to the embodiment of the present invention described with reference to FIG. 1 will be described in more detail.

FIG. 2 is a flowchart illustrating the method of caring for a psychological status based on biometric information according to an embodiment of the present invention.

Referring to FIG. 2, the method of caring for a psychological status based on biometric information according to the embodiment is performed by transmitting information and performing operations between the wearable device 100, the computing device 200, and the user terminal 300.

First, in operation S210, the wearable device 100 may detect real-time biometric information of a user and transmit the detected real-time biometric information to the computing device 200. The wearable device 100 may periodically detect the biometric information of the user wearing the wearable device 100 in a cycle suitable for each type of information, and may transmit the biometric information to the computing device 200 according to a predetermined cycle. The wearable device 100 may acquire biometric information such as EDA, HRV, body temperature, RESP, motion, movement speed, and voice of the user, and real-time positional information of the user.

The wearable device 100 according to the embodiment may periodically transmit the collected information to the computing device 200. The wearable device 100 may repeatedly transmit information to the computing device 200 in a predetermined cycle set in advance as a default value, continuously transmit information in a publish method, and transmit information in a subscription method in response to a periodic request of the computing device 200.

The wearable device 100 according to the embodiment may also transmit information in a predetermined cycle determined based on the user information such as the real-time positional information of the user and the information on the degree of disability of the user. For example, in the case of collecting and utilizing data on positions where a user whose psychological status needs to be cared for feels particularly anxious, when it is determined based on the real-time positional information of the user that the user is located within a specific area, the biometric information of the user may be transmitted in a shorter cycle. In addition, depending on the degree of autism spectrum disorder, the biometric information of the user may be transmitted in a shorter cycle for a user with severe autism spectrum disorder.

The computing device 200 according to the embodiment may acquire the real-time biometric information of the user from the wearable device 100 in operation S220. The computing device 200 according to the embodiment may receive and store user identification information and/or guardian identification information and wearable device identification information corresponding to the user identification information and/or guardian identification information from the user terminal 300 in advance, and utilize the received and stored information to manage various types of information received from the wearable device 100 for each user.

The computing device 200 according to the embodiment may analyze the arousal and valence of the user based on the real-time biometric information in operation S230.

Specifically, the arousal and valence of the user may be analyzed based on at least one of the EDA, HRV, body temperature, RESP, motion, movement speed, and voice information of the user included in the real-time biometric information of the user.

For example, the arousal of the user may be determined based on information including at least EDA among the real-time biometric information of the user, and the valence of the user may be analyzed based on information including at least HRV among the real-time biometric information of the user. As the value of the EDA of the user increases, it may be determined that sweat or the like is formed on the user's skin as a cause, and it may be determined that psychological tension is occurring with the user and the arousal of the user is high. Accordingly, the computing device 200 may determine that the arousal of the user increases as the value of the EDA of the user increases. In addition, it may be determined that, as the value of the body temperature of the user increases, psychological tension is occurring with the user and the arousal of the user is high. In addition, it may be determined that the greater the value of the HRV of the user, the faster the user's heart is beating, which may be determined that a user has high valence because psychological tension or stress is formed. Accordingly, the computing device 200 may determine that the greater the value of the HRV of the user, the higher the valence of the user.

Then, in operation S240, the computing device 200 according to the embodiment may determine the psychological status of the user based on the analyzed arousal and valence of the user. Hereinafter, a detailed method of determining a psychological status of a user will be described with reference to FIG. 3.

Figure 3:
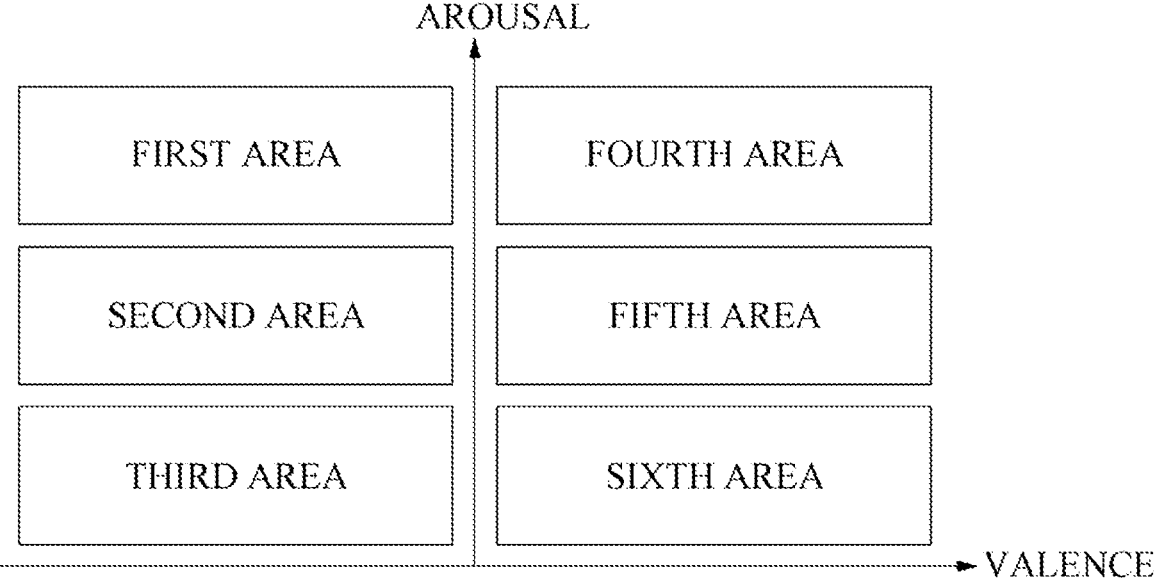
FIG. 3 is a conceptual diagram illustrating a plurality of psychological status areas used in the method of caring for a psychological status based on biometric information according to the embodiment of the present invention.

FIG. 3 is a conceptual diagram illustrating a plurality of psychological status areas used in the method of caring for a psychological status based on biometric information according to the embodiment of the present invention.

The computing device 200 according to the embodiment may set a plurality of psychological status areas (first to sixth areas in FIG. 3) on a two-dimensional plane having the valence and arousal as X and Y axes, respectively. A plurality of psychological status areas may be set having predetermined boundary values of each of arousal and valence, and as illustrated in FIG. 3, a plurality of psychological status areas may not overlap and may have the same area, or may have different sized areas.

The computing device 200 according to the embodiment may set each area using a preset default boundary value and determine the psychological status of the user based on the analyzed arousal and valence of the user values For example, when the positions according to the analyzed arousal and valence of the user values fall within a first area on the 2D plane, the current psychological status of the corresponding user may be determined as the psychological status corresponding to the first area.

In this case, the plurality of psychological status areas may correspond to status values that represent a human psychological status such as "surprise," "angriness," "sadness," "excitement," "happiness" and "composedness" from the first to sixth areas, respectively. For example, the fourth area with high valence and high arousal may correspond to an "excitement" status, and the first area with low valence and high arousal may correspond to a "surprise" status.

For example, the computing device 200 may pre-collect the information on the user, such as the age, sex, weight, and height of the user, from the user terminal 300, and may refer to the boundary values of the arousal and valence for each of the pre-stored psychological status areas based on the pre-collected user information. Accordingly, the computing device 200 may accurately determine the psychological status in a user-customized manner.

Referring back to FIG. 2, in operation S250, the computing device 200 according to the embodiment may transmit the determined psychological status of the user to the user terminal 300 to share the current psychological status of the user with the user or guardian. In addition, the computing device 200 may also transmit and share the real-time biometric information and the analysis results of the arousal and valence to the user terminal 300.

In this case, according to an embodiment, the guardian may monitor the psychological status of the user wearing the wearable device 100 in real time, and may determine the psychological status of the user and directly input control information for pressure control provided from the wearable device 100 to generate a control signal. The control information directly generated by the guardian is transmitted to the wearable device 100 through the computing device 200.

Alternatively, when the guardian wants automatic psychological status care, in operation S260, the computing device 200 may generate the control information based on the determined psychological status of the user. The computing device 200 according to the embodiment may refer to a control information table including pre-matched control information in response to the determined psychological status, and generate control information according to the psychological status of the corresponding user.

Specifically, the computing device 200 may be in a state in which the control information table, which is the control information for controlling the operation of the matched pressure module in response to the psychological status, is stored in advance. Here, the pressure module may be a module such as an air pad capable of applying an external force, such as applying pressure to a user through the wearable device 100, and more specifically, may be a module in which a plurality of modules are combined to perform a function through which the external force can be applied, such as applying the pressure to the user. The wearable device 100 according to the embodiment may include the plurality of pressure modules to press a plurality of parts.

In this case, the control information according to the embodiment may be the information necessary for applying the external force, such as applying the pressure to the user through the operation of the pressure module, and more specifically, may include the information such as the pressure module identification information, the pressure level (intensity), and the pressure time. The pressure module identification information is information indicating a module that applies pressure among a plurality of pressure modules, and for example, when the wearable device 100 includes five pressure modules, the pressure module identification information may include some of 1 (identification information of a first module), 2 (identification information of a second module), 3 (identification information of a third module), 4 (identification information of a fourth module), and 5 (identification information of a fifth module). In addition, the pressure level information is information obtained by leveling the intensity of pressure applied to each pressure module, and the computing device 200 may use a predetermined number of pressure levels. For example, the computing device 200 may use five pressure levels, from level 1 pressure having somewhat weak pressure intensity to level 5 pressure having somewhat strong pressure intensity. Also, the pressure time information may be information on a pressure time maintained in each pressure module.

The computing device 200 may refer to the pre-stored control information table to generate the control information corresponding to the determined psychological status of the user.

Meanwhile, the computing device 200 according to the embodiment may store a default control information table, or in order to generate more accurate control information customized for a user, may generate and use the control information table based on the user information such as the positional information, age, height, weight, sex, and degree of disability of the user.

Hereinafter, a method of generating control information according to an embodiment will be described with reference to FIG. 4.

FIG. 4 is a flowchart illustrating a method of generating control information in the method of caring for a psychological status based on biometric information according to the embodiment.

Referring to FIG. 4, the computing device 200 according to the embodiment may confirm first control information for controlling the operation of the pre-matched pressure module in response to the psychological status determined in operation S261.

That is, the computing device 200 may refer to the pre-stored control information table in the form of Table 1 below to determine the control information corresponding to the determined psychological status of the user. The description of Table 1 below may refer to the six psychological status values that have been described above.

In this case, the computing device 200 may adjust the psychological status of the user based on a deep touch pressure (DTP) method through the wearable device 100, and more specifically, may stimulate the user's parasympathetic nerves by applying an external force such as pressure to the upper body of the user through the user's wearable means, so that the psychological status of the user may be stably adjusted.

Specifically, the DTP method may be referred to as "deep palpation compression," and may be a manner or method of applying pressure to support the psychological status of the user to be stable by applying an external force such as pressure in a distributed form to the body of the user.

TABLE 1

| Psychological Status | Pressure Module | Level (Intensity) | Time |
|---|---|---|---|
| Surprise | 1, 2, 3 | Level 2(3.8) | 15 |
| Angriness | 1, 3 | Level 3(4.2) | 12 |
| Sadness | 2, 3 | Level 1(3.5) | 10 |
| Excitement | 1, 2, 3 | Level 2(3.8) | 15 |
| Happiness | — | — | — |
| Composedness | — | — | — |

Referring to Table 1, the computing device 200 may be in a state in which the pressure module identification information and the information on the pressure intensity and pressure time, which are the control information pre-matched in response to each psychological status, may be stored in advance.

In addition, referring to Table 1, the computing device 200 may generate the control information when the psychological status value corresponding to the estimated psychological status of the user is "surprise" and "excitement," and when the psychological status value corresponding to the psychological status of the user changes from "surprise" and "excitement" to "angriness" and "sadness," the number of pressure modules operated based on Table 1, the pressure intensity, and the pressure time may increase or decrease.

Specifically, according to Table 1, when the determined psychological status of the user is "surprise," the computing device 200 may apply the pressure to the user through operations of the first pressure module, the second pressure module, and the third pressure module included in the psychological control device. In this case, the computing device 200 may apply the pressure to the user at pressure intensity "3.8" for time "15" based on the first pressure module, the second pressure module, and the third pressure module.

In this case, the pressure intensity and the pressure time described in Table 1 may be represented as a unit for the pressure intensity and the pressure time, and may be represented as a separate unit obtained by converting units of the pressure intensity and pressure time. With this method, the computing device 200 may confirm the first control information, which is the pre-matched control information, in response to the estimated psychological status of the user.

Thereafter, the computing device 200 may confirm the second control information which is the control information on the operation history of the pre-controlled pressure module in response to the estimated psychological status of the user based on the operation history in operation S262.

Specifically, when the first control information is generated, the computing device 200 may check the operation history of the pressure module in response to the estimated psychological status of the user. That is, the computing device 200 may accumulate and store the control information through which the content of the operation history of the pressure module in response to the determined psychological status of the user can be checked in the psychological control device.

When the estimated psychological status of the user value by the psychological control device is "surprise," the computing device 200 according to the embodiment may confirm the control information in the state in which the psychological status of the corresponding user is "surprise," which may be referred to as the second control information. In this case, the second control information may have items such as "psychological status," "pressure module," "intensity," and "time" in the same format as the first control information.

However, when the determined psychological status of the user in the computing device 200 is the first time or the psychological control device of the user is used for the first time, there may be no content about the operation history of the pressure module in response to the determined psychological status of the user. In this situation, the computing device 200 may check past control information through which the content of the operation history of the pressure module in response to the psychological status can be checked.

Thereafter, in operation S263, the computing device 200 may compare the confirmed first control information and second control information and generate the control information based on a result of the comparison.

Specifically, the psychological control device may compare values between a plurality of items included in the first control information and a plurality of items included in the second control information, and generate final control information in which values between the plurality of items included in the first control information and the plurality of items included in the second control information are reflected based on a preset calculation method.

For example, the computing device 200 may select the overlapping "pressure modules" among the types of "pressure modules" included in the first control information and the types of "pressure modules" included in the second control information, and may reflect the identification information of the selected "pressure module" in the "pressure module" item of the final control information.

In addition, the computing device 200 may calculate an average intensity value of the "level (intensity)" value included in the first control information and the "level (intensity)" value included in the second control information, and reflect the calculated average intensity value in the "level (intensity)" item of the final control information. In addition, the computing device 200 may calculate a value of an average time for a value of "time" included in the first control information and a value of "time" included in the second control information, and reflect the calculated value of the average time in the term "time" of the final control information.

Referring back to FIG. 2, the computing device 200 according to the embodiment may transmit the generated control information to the wearable device 100. In addition, the computing device 200 may transmit the generated control information to the user terminal 300, and then transmit the control information to the wearable device 100 only when control approval is received from the user terminal 300.

Thereafter, in operation S270, the wearable device 100 according to the embodiment may perform the pressure control based on the received control information.

Specifically, it is possible to control the pressure module included in the wearable device based on the values of the "pressure module," "level (strength)," and "time," which are the plurality of items included in the final control information, so that the pressure module included in the psychological control device may be operated Thereafter, in operation S280, the computing device 200 according to the embodiment may detect the reaction information of the user to the performed pressure control. The reaction information according to the embodiment indicates the user's reaction to the performed pressure control, and may include the biometric information of the user detected for a predetermined period after the control information is transmitted. Alternatively, the reaction information may include the biometric information of the user detected after the control information is transmitted and a predetermined time has elapsed.

The computing device 200 according to the embodiment may generate a psychological care model trained using the reaction information of the user received from the wearable device 100 in operation S290. Specifically, the computing device 200 may generate the psychological care model trained using at least one of the real-time biometric information of the user acquired in operation S220, arousal and valence of the user analyzed in operation S230, the psychological status of the user determined in operation S240, the control information generated in operation S260, and the reaction information collected in operation S280 in response to the at least one piece of information.

Hereinafter, the method of caring for a psychological status by converting the reaction information of the user into big data will be described with reference to FIGS. 5 and 6.

Figure 5:
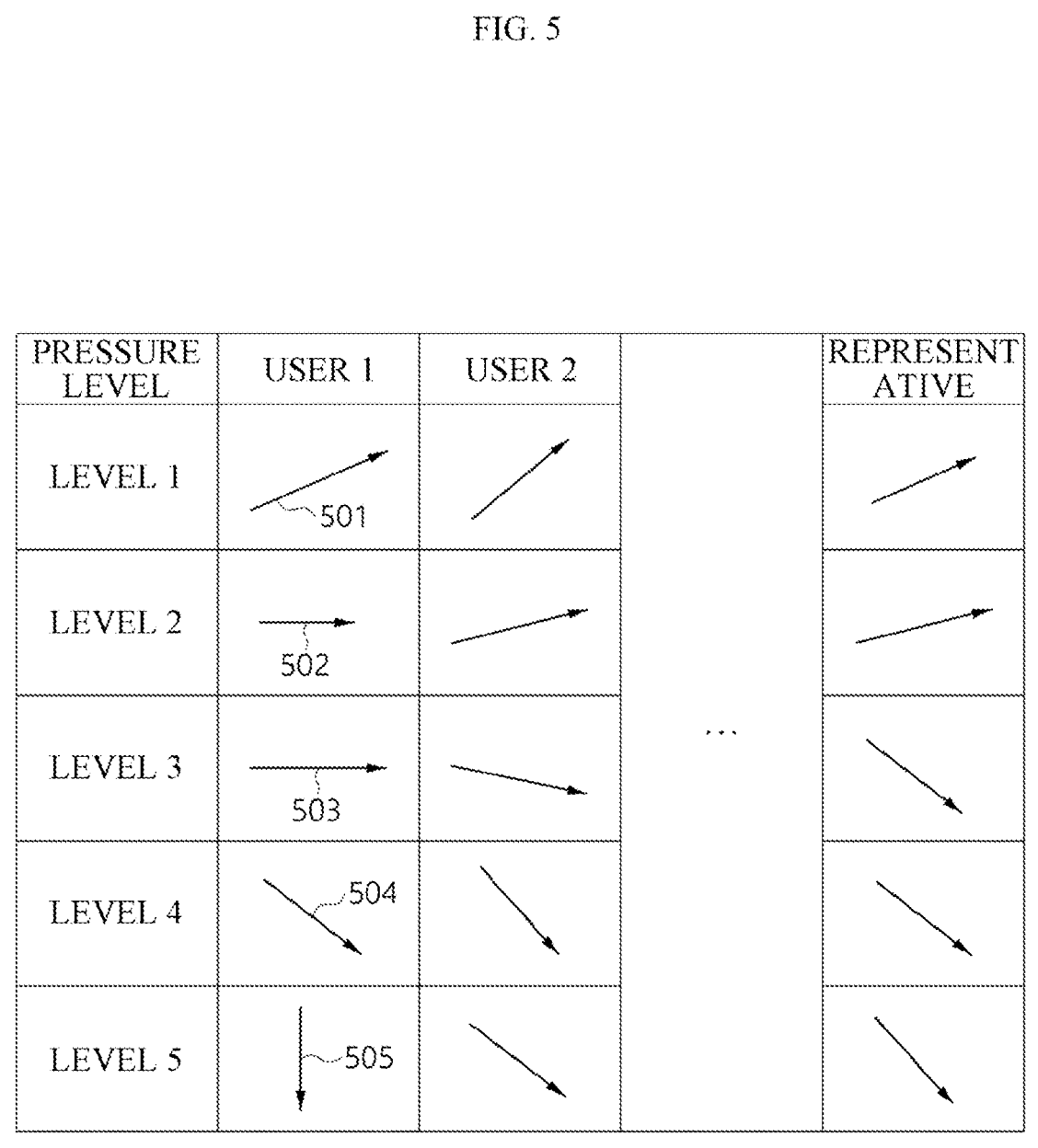

FIG. 5 is a diagram illustrating a reaction information table of a user used in the method of caring for a psychological status based on biometric information according to the embodiment.

The computing device 200 according to the embodiment may generate a reaction information table representing the history information on the reaction information of the user and use the generated reaction information table to generate the control information for the psychological status care.

Specifically, when the pressure control is performed on the user according to the control information in the method of caring for a psychological status based on biometric information according to the embodiment, the computing device 200 may acquire the reaction information of the user detected in the wearable device 100. The reaction information according to the embodiment indicates the biometric reaction of the user to the performed pressure control, and may include the biometric information of the user detected for a predetermined period after the control information is transmitted.

In this case, the computing device 200 may use the reaction information to generate the reaction vector representing the change rate of valence and arousal for a predetermined time according to the pressure level. For example, the reaction vector of the user may use the coordinates (valence value and arousal value) according to the biometric information before the pressure control is performed on the two-dimensional plane having the valence value and the arousal value as the X value and the Y value, respectively, as the starting point, and the reaction vector of the user may be represented by a vector using the coordinates (valence value and arousal value) according to the reaction information after the pressure control is performed as the end point.

The computing device 200 according to the embodiment may generate a reaction information table representing the history information on reaction information of the corresponding user by generating a reaction vector and converting the reaction vector into big data whenever the pressure control is performed. The reaction information table according to the embodiment may generate data for each user and may include the reaction history vectors of the user for each level. For example, the reaction history vector included in the table may be an average vector of each reaction vector for the corresponding level of the corresponding user, or may be a most frequent vector of each reaction vector, but is not limited thereto.

Referring to FIG. 5, the computing device 200 may generate the reaction information table including a reaction history vector 501 of level 1, a reaction history vector 502 of level 2, a reaction history vector 503 of level 3, a reaction history vector 504 of level 4, and a reaction history vector 505 of level 5 for user 1. For example, user 1 may have a reaction history in which the valence and arousal for the pressure level of level 1 increases, a reaction history in which only the valence for the pressure level of level 2 increases, a reaction history in which only the valence for the pressure level of level 4 increases, a reaction history in which only the valence for the pressure level of level 4 increases and the arousal for the pressure level of level 4 decreases, and a reaction history in which only the arousal for the pressure level of level 5 decreases.

The computing device 200 according to the embodiment may manage history information for each user, and may generate representative history information by integrating history information for a plurality of users. For example, the representative history information may be generated based on reaction history vectors for each level of the plurality of users, and may be a most frequent average vector of each reaction history vector or a most frequent vector of each reaction history vector, but is not limited thereto.

The computing device 200 according to the embodiment may use representative history information when it does not have history information because there is no data or insufficient data on a user wearing the wearable device 100.

In this case, the computing device 200 may use representative history information for all users, or may generate and use representative history information for a similar group of the corresponding user. For example, the similar group may be a group to which the corresponding user belongs among a plurality of groups classified according to at least one type of user information such as an age, a height, a weight, a sex, disability information, a disability type, and a disease type of the user.

Hereinafter, a method of caring for a psychological status using a reaction information table of FIG. 5 will be described with reference to FIG. 6.

Figure 6:
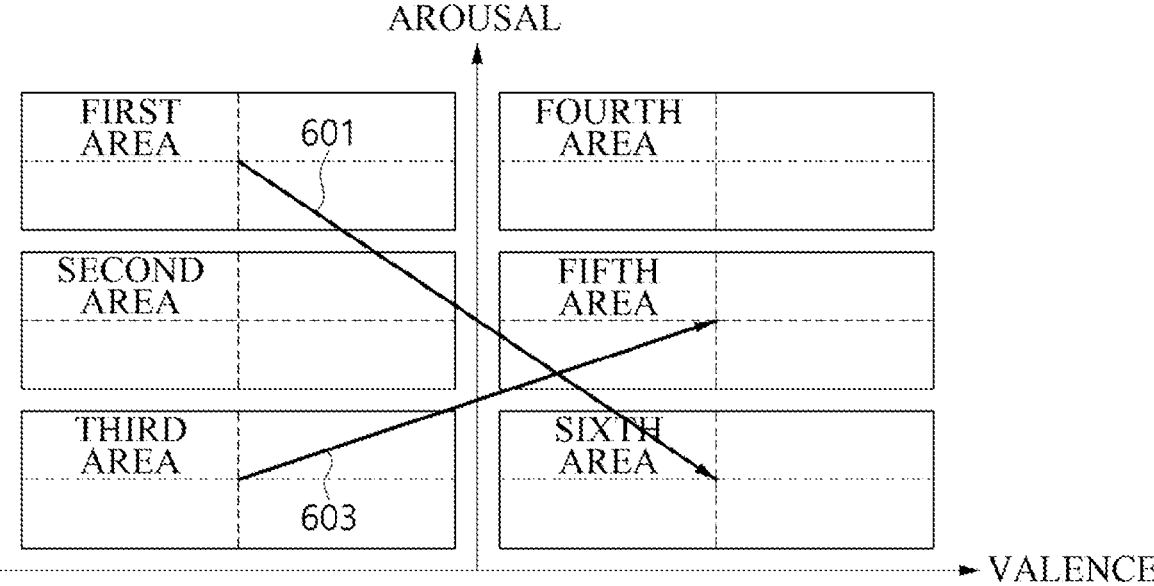
FIG. 6 is a diagram for describing a method of caring for a psychological status based on biometric information using a reaction information table according to an embodiment.

FIG. 6 is a diagram for describing a method of caring for a psychological status based on biometric information using a reaction information table according to an embodiment. A coordinate plane of FIG. 6 may be the same as the coordinate plane illustrating the plurality of psychological status areas of FIG. 3.

In an embodiment, the computing device 200 may determine an adjustment vector for a plurality of psychological status areas set with respective predetermined boundary values of the arousal and valence, and may use the determined adjustment vector for the control information generation.

Specifically, the computing device 200 may generate the adjustment vectors for each of the plurality of psychological status areas set on the two-dimensional plane having the valence and arousal as the X and Y axes, respectively. The adjustment vector represents a desirable change in psychological status with respect to the psychological status area in which care is required, and may represent a desired position of a target psychological status area with respect to a position of a current psychological status area. According to an embodiment, a target psychological status area for a current psychological status area may be determined through an opinion of an expert such as a doctor or big data.

For example, the target psychological status area for the first area (psychological status "surprise") may be the sixth area (psychological status "composedness"), and an adjustment vector 601 for the first area may be a vector having a position of the current psychological status area (first area) as a starting point and a position of the target psychological status area (sixth area) as an end point. In this case, a position of a area is a center position of each area, and may be one of a point indicating the boundary of the area or a point where diagonal lines cross in the polygon or a vertex in the polygon, but is not limited thereto.

In addition, the target psychological status area for the third area (psychological status "sadness") may be the fifth area (psychological status "happiness"), and an adjustment vector 603 for the third area may be a vector having a position of the current psychological status area (third area) as a starting point and a position of the target psychological status area (fifth area) as an end point. In FIG. 6, only the adjustment vectors for the first area and the second area are illustrated for convenience of description, but other psychological status areas may also have the target psychological status area and the adjustment vector.

In an embodiment, the computing device 200 may generate control information to be used for the psychological status care based on the adjustment vectors determined for each psychological status area described above.

Specifically, the computing device 200 may generate the control information by comparing the adjustment vectors determined for each psychological status area with the reaction history vector of the reaction information table of FIG. 5. The computing device 200 may acquire the adjustment vector for the psychological status area determined for the user, select the reaction history vector most similar to the corresponding adjustment vector among the reaction history vectors of the corresponding user with reference to the reaction information table, and generate the control information based on the selected reaction history vector. For example, the reaction history vector most similar to the adjustment vector may be a vector having a largest dot product value with the adjustment vector.

For example, the computing device 200 according to the embodiment may determine the pressure level of the control information based on the pressure level of the selected reaction history vector, and determine the pressure time of the control information based on the size of the selected reaction history vector. Referring to FIGS. 5 and 6, when the psychological status of user 1 is determined to be "surprise," the computing device 200 may select the reaction history vector 504 most similar to the adjustment vector 601 of the first area (psychological status "surprise"), determine the pressure level of the control information based on the pressure level ("level 5") of the selected reaction history vector 504, and determine the pressure time of the control information based on the size of the selected reaction history vector 504. For example, when the size of the reaction history vector 504 is greater than the size of the adjustment vector 601, the computing device 200 may determine the time of control information shorter than the predetermined time required to detect the reaction information, and when the size of the reaction history vector 504 is smaller than the size of the adjustment vector 601, the computing device 200 may determine the control information time longer than a predetermined time required to detect the reaction information.

The computing device 200 according to the embodiment may generate control information based on the adjustment vector and history information accumulated based on the above-described reaction information, and adaptively and more accurately care for the psychological status of the user.

Hereinafter, a psychological care model for implementing the method of caring for a psychological status using an artificial neural network in relation to operation S290 of FIG. 2 will be described in detail with reference to FIG. 7.

Figure 7:
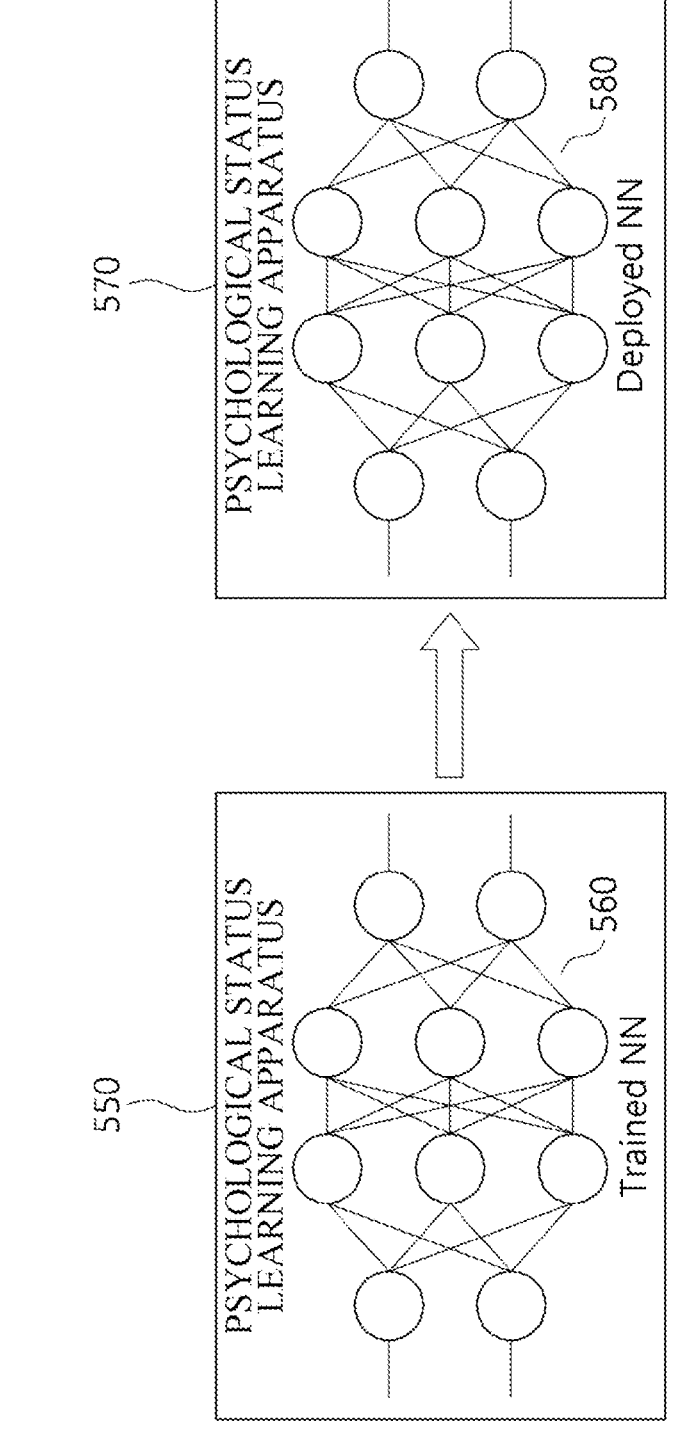
FIG. 7 is a diagram for describing a method of caring for a psychological status based on biometric information using an artificial neural network according to an embodiment.

FIG. 7 is a diagram for describing a method of caring for a psychological status based on biometric information using an artificial neural network according to an embodiment.

Referring to FIG. 7, the computing device 200 according to the embodiment may care for the psychological status of the user using the pre-trained artificial neural network-based model, and may be configured to include a psychological status learning device 750 and a psychological status care device 770. The computing device according to this embodiment may be the same device as the computing device 200 of FIG. 1.

Referring to FIG. 7, the computing device 200 according to the embodiment corresponds to a computing device having various processing functions such as functions of generating a neural network, training (or learning) a neural network, or retraining a neural network. For example, the psychological status learning device 750 may be implemented in various types of devices such as a personal computer (PC), a server device, and a mobile device, and may be implemented by components in the computing device 200 of FIG. 1.

The psychological status learning device 750 may generate a trained neural network 760 by repeatedly training (learning) a given initial neural network. For example, the psychological status learning device 750 according to the embodiment may perform learning using user information and health examination result information corresponding to the user information. Generating the trained neural network 760 may mean determining the neural network parameters. Here, parameters may include, for example, various types of data input/output to/from the neural network, such as input/output activations, weights, and biases of the neural network. As the repetitive training of the neural network progresses, the parameters of the neural network may be tuned to calculate a more accurate output for a given input.

The psychological status learning device 750 may transfer the trained neural network 760 to the psychological status care device 770. The psychological status care device 770 may be included in a mobile device, an embedded device, or the like. The psychological status care device 770 may be dedicated hardware for driving the neural network, and may be implemented by components in the computing device 200 of FIG. 1.

The psychological status care device 770 may drive the trained neural network 760 itself or drive the neural network 780 processed by quantizing the trained neural network 760. For example, the psychological status care device 770 according to the embodiment may extract a list of recommended examination items by inputting user information to the pre-trained artificial neural network-based model. The psychological status care device 770 that drives the processed neural network 780 may be implemented in a separate and independent device from the psychological status learning device 750. However, the psychological status care device 770 is not limited thereto and may be implemented in the same device as the psychological status learning device 750.

Hereinafter, a detailed method of performing psychological status care based on biometric information through the psychological status learning device 750 and the psychological status care device 770 will be described with reference to FIG. 8.

Figure 8:
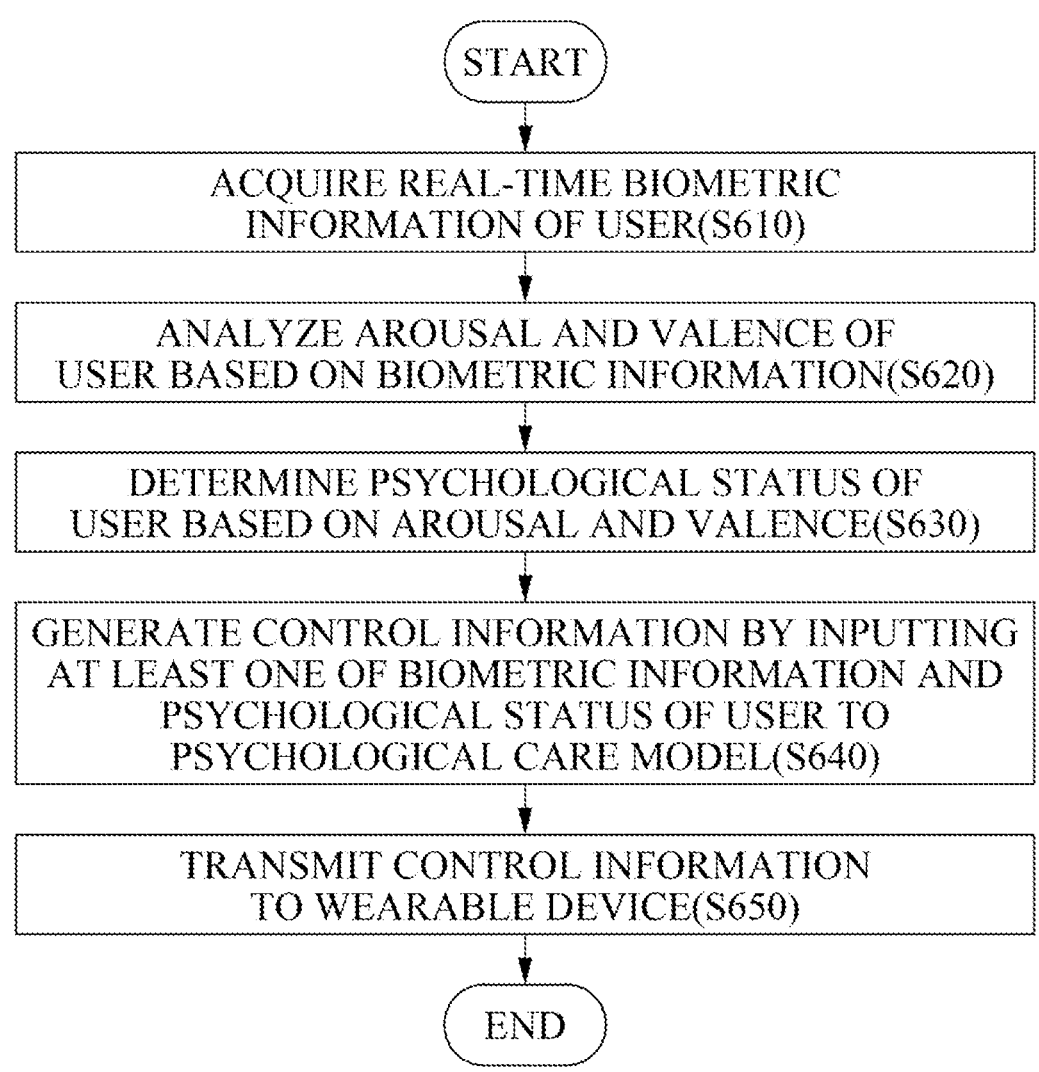
FIG. 8 is a flowchart illustrating the method of caring for a psychological status based on biometric information using an artificial neural network according to the embodiment.

FIG. 8 is a flowchart illustrating the method of caring for a psychological status based on biometric information using an artificial neural network according to the embodiment.

The method of caring for a psychological status based on biometric information using an artificial neural network described in FIG. 8 may be performed by the computing device 200 of FIG. 1, and unless otherwise arranged, specific methods performed in the method of caring for a psychological status based on biometric information according to the embodiment of FIG. 2 may be used instead. Hereinafter, each operation will be described mainly based on the computing device 200.

Referring to FIG. 8, the computing device 200 according to the embodiment may acquire the real-time biometric information of the user in operation S810. The computing device 200 may acquire the real-time biometric information of the user from a wearable device worn by the user.

Hereinafter, the computing device 200 according to the embodiment may analyze the arousal and valence of the user based on the real-time biometric information of the user in operation S230. The computing device 200 may analyze the arousal and valence of the user using the method used in operation S230 of FIG. 2.

Hereinafter, in operation S830, the computing device 200 according to the embodiment may determine the psychological status of the user based on the analyzed arousal and valence of the user. The computing device 200 may determine the psychological status of the user by the method used in operation S240 of FIG. 2, or may determine the psychological status of the user using an artificial neural network.

Specifically, in the case of using the artificial neural network, the computing device 200 may input the real-time biometric information to the psychological care model to set the boundary value of the plurality of areas positioned on the two-dimensional plane having the valence and arousal as the X and Y axes, respectively.

In this case, the psychological care model may be trained using the real-time biometric information of the user, the psychological status of the user, the control information, and the reaction information of the corresponding user that are continuously acquired according to the repeated execution of the method of caring for a psychological status in FIG. 2, and may use the artificial neural network through data accumulation to more accurately determine the psychological status of the user based on the arousal and valence.

The computing device 200 may analyze the arousal and valence of the user with real-time biometric information, and based on this, select one of a plurality of areas classified by the boundary value determined by the psychological care model to determine the psychological status of the user.

Thereafter, the computing device 200 according to the embodiment may generate the control information using the previously acquired information in operation S840. The computing device 200 may generate the control information by the method used in operation S240 of FIG. 2, or may determine the psychological status of the user by using the artificial neural network.

Specifically, when using the artificial neural network, the computing device 200 may input at least one of the acquired real-time biometric information of the user and the psychological status of the user to the psychological care model to generate the control information.

In this case, the psychological care model may be trained using the real-time biometric information of the user, the psychological status of the user, the control information, and the reaction information of the corresponding user that are continuously acquired according to the repeated execution of the method of caring for a psychological status in FIG. 2, and may use the artificial neural network through the data accumulation to more accurately generate the control information based on the real-time biometric information of the user.

In addition, not only does the computing device 200 according to the embodiment include the real-time biometric information of the user, the psychological status of the user, the control information, and the reaction information of the user corresponding thereto, but at least one type of the user information such as the real-time positional information, age, height, weight, sex, degree of disability, and the like of the user matched to correspond to the corresponding information may also be used to train the psychological care model described above.

Accordingly, the computing device 200 may determine the psychological status of the user based on the psychological care model that performs more accurate analysis customized for the user to generate the control information.

Thereafter, the computing device 200 according to the embodiment may transmit the generated control information to the wearable device 100 in operation S850 so that the wearable device 100 may use the control information for the user to perform the pressure control. In addition, the computing device 200 may transmit the generated control information to the user terminal 300 so that a user or a guardian may confirm not only the real-time biometric information of the user but also the control information generated based thereon.

The method of caring for a psychological status based on biometric information according to the embodiment has been described above as being mostly performed in the computing device 200, but it may not necessarily be limited thereto. That is, some of each operation of the method of caring for a psychological status performed by the above-described computing device 200 may be performed by a driving unit of the wearable device 100 including a processor.

In other words, although the psychological control device described in the present invention is described as performing most of the operations in the psychological control device itself, when some operations are performed in the analysis and control server, the psychological control method of the present invention may be performed by transmitting or receiving the information generated or managed by the psychological control device to or from the analysis and control server.

Figure 9:
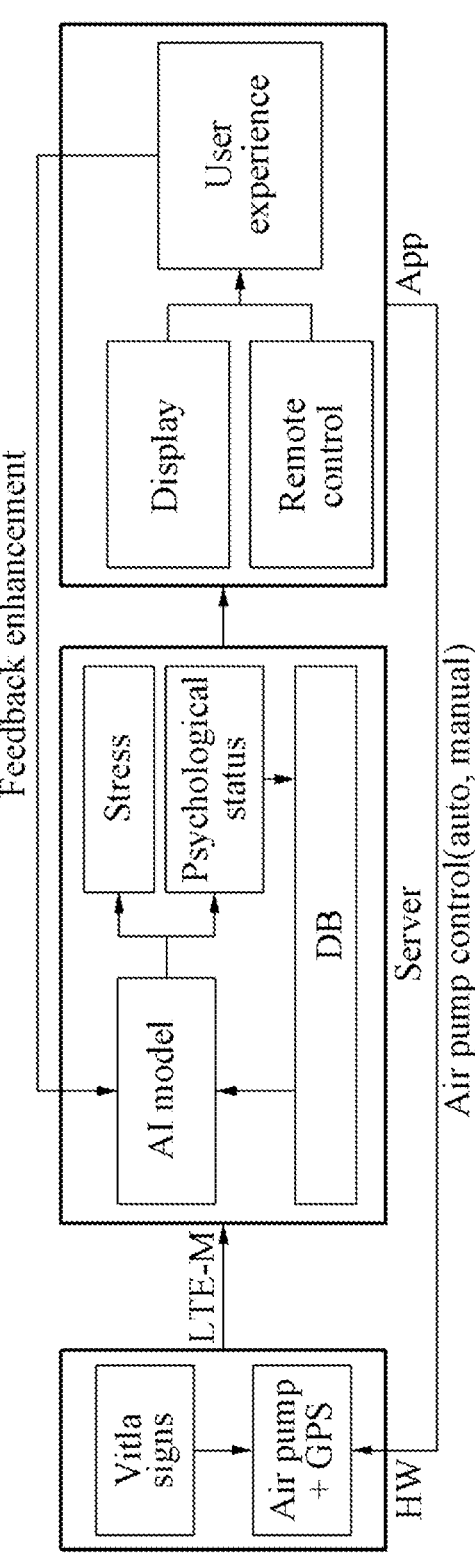
FIG. 9 is a conceptual diagram illustrating a system for performing a method of caring for a psychological status based on biometric information according to an embodiment.

FIG. 9 is a conceptual diagram illustrating a system for performing a method of caring for a psychological status based on biometric information according to an embodiment.

Referring to FIG. 9, the computing device, the wearable device, and the user terminal performing the method of caring for a psychological status based on biometric information according to an embodiment may constitute a system as shown in FIG. 9.

Specifically, as illustrated in FIG. 9, the system may include a hardware (HW) part such as the wearable device and the server corresponding to the computing device, and further include an application (APP) for providing services for a user, such as providing various types of information through the user terminal.

Here, the wearable device (HW), which may be the hardware part, and the computing device, which is a server performing the analysis and control, may transmit or receive necessary information based on mutual communication, and in more detail, may communicate with each other based on communication such as LTE-machine type communication (LTE-M).

Basically, as illustrated in FIG. 9, the wearable device (HW) may serve to acquire information related to vital signs, and perform a pressure control operation in the method of caring for a psychological status of the present invention based on an air pump, a GPS module, and the like.

In addition, as illustrated in FIG. 9, the analysis and control server, which is the computing device, may include a module for analyzing an artificial intelligence (AI) model, a database (DB, database), and a module that analyzes a psychological status and the like for analyzing a user's stress and may connect the modules or models to each other based on communication or physically connect the modules or models to transmit or receive information to or from each other.

In addition, as illustrated in FIG. 9, the application (APP) for the user installed in the user terminal may include a display means capable of providing an interface to a user or outputting and providing information, and further include a module for remote control. In this process, the psychological control device may transmit information on the user's reaction (or user experience), etc., to an AI model of the analysis and control server through the application to perform a feedback procedure.

In this case, a procedure such as remote control may be performed based on BLE( ) or LTE( ) In addition, in the application, services such as a user registering as a member may be provided to the platform of the psychological control system of the present invention, and services through which members such as users can be managed may be provided on the platform of the psychological control system.

The methods according to the present invention may be implemented in the form of program commands that may be executed through various computer means and may be recorded in a computer-readable recording medium. The computer-readable recording medium may include a program command, a data file, a data structure, or the like alone or in combination. Program instructions recorded on the computer-readable medium may be specially designed and configured for the present invention or may be known and usable to those skilled in the art of computer software.

Examples of the computer-readable medium may include hardware devices specially configured to store and execute program instructions, such as a ROM, a RAM, a flash memory, and the like.

In particular, examples of the program commands include a high-level language code capable of being executed by a computer using an interpreter, or the like, as well as a machine language code made by a compiler. The above-described hardware device may be constituted to be operated as one or more software modules in order to perform an operation according to the present invention, and vice versa.

In addition, the above-described method or apparatus may be implemented by combining all or some of its components or functions, or may be implemented separately.

Although exemplary embodiments of the present invention have been disclosed hereinabove, it may be understood by those skilled in the art that the present invention may be variously modified and altered without departing from the scope and spirit of the present invention described in the following claims.

The invention claimed is:

1. A method of caring for a psychological status of a user based on biometric information, performed by a computing device, the method comprising:
    acquiring, via a wearable device worn by the user, real-time biometric information of the user;
    analyzing, via the computing device, an arousal level and a valence level of the user based on the acquired real-time biometric information, wherein analyzing the arousal level comprises processing at least electrodermal activity data from the biometric information, and analyzing the valence level comprises processing at least heart rate variability data from the biometric information;
    determining a first psychological status of the user based on the analysis result of the arousal and valence levels of the user, by identifying which of a plurality of predefined psychological status areas on a two dimensional plane having valence and arousal axes includes the analyzed arousal and valence levels, each of the plurality of areas corresponding to a distinct psychological status, and assigning the psychological status corresponding to the identified area as the first psychological status of the user;
    generating, on the two-dimensional plane in which the valence level corresponds to an X-axis and the arousal level corresponds to a Y-axis, a first reaction history vector having a starting point defined by coordinate values including an X value and a Y value measured before pressure control corresponding to a first pressure level is performed, and an ending point defined by coordinates values including an X value and a Y value derived from reaction information of the user after the pressure control corresponding to the first pressure level is performed;
    generating a second reaction history vector having a starting point defined by coordinate values including an X value and a Y value measured before pressure control corresponding to a second pressure level is performed, and an ending point defined by coordinate values including an X value and a Y value derived from reaction information of the user after the pressure control corresponding to the second pressure level is performed;
    generating an adjustment vector having starting point coordinates to a center position of a first psychological status area among the plurality of predefined psychological status areas, and an ending point corresponding to a center position of a target psychological status area;
    selecting, from among the first reaction history vector and the second reaction history vector, a reaction history vector that is more similar to the adjustment vector;
    wherein the reaction history vector that is more similar to the adjustment vector is determined as a reaction history vector having a largest dot product value with the adjustment vector; and
    based on the selection reaction history vector, generating a control information including a pressure level corresponding to the selected reaction history vector and a pressure time, the pressure time being determined based on a size of the selected reaction history vector; and
    controlling an air pad based on the control information.

2. The method of claim 1, wherein analyzing the arousal level and the valence level further comprises processing at least one additional biometric signal selected from body temperature, respiration, motion, position, movement speed, and voice information.

3. The method of claim 1, wherein the plurality of predefined psychological status areas comprise six areas on the two-dimensional plane.

4. The method of claim 1, wherein generating the first control information comprises referring to a pre-stored control information table that maps a psychological status of the user to pressure control parameters including at least one of a pressure level, a pressure intensity, a pressure time, and identification information of a pressure module.

5. The method of claim 1, further comprising: obtaining reaction information of the user from the wearable device; generating a reaction vector corresponding to the reaction information; generating, for each pressure level, a reaction history vector based on the reaction vector; and generating for each psychological status area on the two dimensional plane an adjustment vector, wherein generating the control information is based at least in part on comparing the generated reaction history vectors of the user with the adjustment vector for the area corresponding to the first psychological status.

6. The method of claim 1, further comprising: acquiring reaction information of the user from the wearable device; and generating a psychological care model trained using the real-time biometric information of the user, the first psychological status of the user, the control information, and the reaction information of the user corresponding thereto, wherein the reaction information includes biometric information of the user detected for a predetermined time after transmitting the control information to the wearable device.

7. The method of claim 6, wherein determining the first psychological status comprises inputting the real-time biometric information into the psychological care model, setting boundary values of the plurality of psychological status areas on the two-dimensional plane, determining one of the plurality of areas based on the analyzed arousal and valence levels, and assigning the psychological status corresponding to the determined area as the first psychological status of the user.

8. The method of claim 1, wherein generating the control information comprises inputting at least one of the real-time biometric information and the first psychological status into a psychological care model, and the control information includes at least one of a pressure level, a pressure time, and identification information of a pressure module.

9. The method of claim 1, further comprising: acquiring user information including at least one of positional information of the user and an age, a height, a weight, a sex, and a degree of disability of the user from the wearable device and/or a user terminal; generating a control information table including control information corresponding to the psychological status of the user based on the positional information and the user information; and generating the control information according to the first psychological status by referring to the generated control information table.

10. A computing device for caring for a psychological status of a user based on biometric information, the computing device comprising:
a processor; and a memory storing at least one instruction that, when executed by the processor, cause the computing device to perform operation to:
acquire, via a wearable device worn by the user, real-time biometric information of the user;
analyze, via the computing device, an arousal level and a valence level of the user based on the acquired real-time biometric information, wherein analyzing the arousal level comprises processing at least electrodermal activity data from the biometric information, and analyzing the valence level comprises processing at least heart rate variability data from the biometric information;
determine a first psychological status of the user based on the analysis result of the arousal and valence levels of the user, by identifying which of a plurality of predefined psychological status areas on a two dimensional plane having valence and arousal axes includes the analyzed arousal and valence levels, each of the plurality of areas corresponding to a distinct psychological status, and assigning the psychological status corresponding to the identified area as the first psychological status of the user;
generate, on the two-dimensional plane in which the valence level corresponds to an X-axis and the arousal level corresponds to a Y-axis, a first reaction history vector having a starting point defined by coordinate values including an X value and a Y value measured before pressure control corresponding to a first pressure level is performed, and an ending point defined by coordinates values including an X value and a Y value derived from reaction information of the user after the pressure control corresponding to the first pressure level is performed;
generate a second reaction history vector having a starting point defined by coordinate values including an X value and a Y value measured before pressure control corresponding to a second pressure level is performed, and an ending point defined by coordinate values including an X value and a Y value derived from reaction information of the user after the pressure control corresponding to the second pressure level is performed;
generate an adjustment vector having starting point coordinates to a center position of a first psychological status area among the plurality of predefined psychological status areas, and an ending point corresponding to a center position of a target psychological status area;
select, from among the first reaction history vector and the second reaction history vector, a reaction history vector that is more similar to the adjustment vector;
wherein the reaction history vector that is more similar to the adjustment vector is determined as a reaction history vector having a largest dot product value with the adjustment vector; and
based on the selection reaction history vector, generating a control information including a pressure level corresponding to the selected reaction history vector and a pressure time, the pressure time being determined based on a size of the selected reaction history vector; and
control an air pad based on the control information.

* * * * *